United States Patent [19]

Naarmann et al.

[11] 4,074,032
[45] Feb. 14, 1978

[54] MANUFACTURE OF HEAT-STABLE BROMINATED OLIGOMERS OF MONOVINYL-AROMATIC COMPOUNDS

[75] Inventors: Herbert Naarmann, Wattenheim; Klaus Penzien, Frankenthal; Hermann Gausepohl, Mutterstadt, all of Germany

[73] Assignee: BASF Aktiengesellschaft, Ludwigshafen, Germany

[21] Appl. No.: 705,278

[22] Filed: July 14, 1976

[30] Foreign Application Priority Data

Aug. 22, 1975 Germany .............................. 2537385

[51] Int. Cl.$^2$ ........................... C08F 8/20; C08F 8/22; C08F 8/04
[52] U.S. Cl. ...................................... 526/44; 260/667; 526/25; 526/26; 526/43; 528/487
[58] Field of Search ...................... 526/44, 25, 26, 43; 260/667; 528/487

[56] References Cited

U.S. PATENT DOCUMENTS

| | | | |
|---|---|---|---|
| 3,039,977 | 6/1962 | Ingram | 526/44 |
| 3,607,989 | 9/1971 | Sonnabend | 526/26 |

FOREIGN PATENT DOCUMENTS

| | | | |
|---|---|---|---|
| 364,873 | 1/1931 | United Kingdom | 526/44 |
| 841,946 | 4/1957 | United Kingdom | 526/44 |

*Primary Examiner*—William F. Hamrock
*Attorney, Agent, or Firm*—Keil, Thompson & Shurtleff

[57] ABSTRACT

A process for the manufacture of heat-stable, brominated oligostyrenes by brominating selectively hydrogenated oligostyrenes in halogenated solvents in the presence of Lewis acids at from $-25°$ to $+20°$ C. The brominated oligomers are highly heat-stable and can be processed, by themselves or as components of mixtures with other thermoplastics, to give various shaped articles.

5 Claims, No Drawings

MANUFACTURE OF HEAT-STABLE BROMINATED OLIGOMERS OF MONOVINYL-AROMATIC COMPOUNDS

The present invention relates to a process for the manufacture of heat-stable, brominated oligostyrenes by bromination of selectively hydrogenated oligostyrenes.

Numerous attempts have already been made to brominate polystyrenes directly. However, the conventional processes present a variety of difficulties. Thus, when brominating polystyrene, it is the polymer main chain which is attacked, and this results in considerable changes in viscosity. For example, when using the conventional technique of bromination in chlorinated solvents in the cold, using Lewis acid catalysts, polystyrene gives heavily discolored reaction products of increased viscosity. At bromine contents of more than 20%, these products are obtained in a swollen or cross-linked state and cannot be processed to give the light-colored and heat-stable products required for industrial purposes.

The bromination of dissolved polystyrene with N-bromosuccinimide and peroxides, as described in Makromol. Chem. 52 (1962), 70–78, gives products of reduced molecular weight and a maximum bromine content of 30% by weight, the bromine being bonded to aliphatic structures. Because of the bromination and scission of the polymer chain, the brominated oligomers thus obtained do not have high heat stability. French Pat No. 1,245,832 discloses the bromination of polystyrene in aqueous emulsions. This method only gives products having bromine contents of up to 10% by weight, and low heat stability.

It was surprising and in no way foreseeable that the bromination of the selectively hydrogenated oligomers of monovinyl-aromatic compounds would give heat-stable, brominated products, since, according to the prior art, the direct bromination of styrene polymers has hitherto only given products of low heat stability and the reaction of bromine with monomeric isopropylbenzene or with branched higher alkylbenzenes does not give the corresponding nuclear-brominated branched alkylenbenzenes. For the purposes of the invention, brominated oligomers of monovinyl-aromatic compounds are described as heat-stable if they contain the bromine exclusively in the aromatic nucleus and, after 10 minutes' heating in bulk at from 240° to 340° C do not eliminate any hydrogen bromide and show no significant discoloration, if any.

All the processes for the direct bromination of styrene polymers have hitherto only given products of low, unsatisfactory, heat stability. Heat-stable, nuclear-brominated styrene polymers have hitherto only been obtainable indirectly. Thus, German Patent 1,570,395 discloses a process by means of which the desired heat-stable polymers are obtainable from nuclear-brominated monohaloethylbenzene, via the intermediate stage of nuclear-halogenated styrenes, by treatment with bases and free radical initiators. For this method, 2-halogenoethylbenzene must be available as the starting product, and its manufacture entails additional reaction steps. This process is also too expensive because it necessitates splitting off the side-chain halogen in order to produce a polymerizable vinyl monomer.

It is an object of the present invention to provide a very simple and economical process for the manufacture of brominated polymerization products of styrene which have high heat stability.

We have found that this object is achieved by a process wherein selectively hydrogenated styrene oligomers are brominated under specific conditions.

Accordingly, the invention relates to a process for the manufacture of heat-stable, brominated oligomers of monovinyl-aromatic compounds, wherein the selectively hydrogenated oligomers of the monovinyl-aromatic compounds are dissolved in halogenated solvents and are reacted with bromine, in the presence of Lewis acids as catalysts, at from −25° C, to 20° C, after which the reaction solution is washed free from bromide with water, by conventional methods, and the brominated reaction product is then isolated from the reaction solution.

Suitable oligomers of monovinyl-aromatic compounds are in particular the homo-oligomers of styrene and of the nuclear-alkylated styrenes. Suitable nuclear-alkylated styrenes are above all those which contain one or more alkyl groups which are not branched at the carbon atom joined to the nucleus, e.g. vinyltoluene, vinylethylbenzene and vinylpropylbenzene. The co-oligomers of styrene with α-methylstyrene and with the nuclear-alkylated styrenes may also be used in the same way as the homo-oligomers. Butadiene, isoprene and/or chloroprene can also be used as co-monomers for the manufacture of the oligomers to be employed according to the invention. However, the use of the homo-oligomers of styrene is preferred.

Styrene oligomers per se have been disclosed and are described, e.g., in German Laid-Open application DOS 2,239,356 and British Patent 549,930. They can be manufactured by conventional methods, e.g. by oligomerization of the monomers in bulk or in solution. This oligomerization is carried out either in the presence of conventional free radical initiators at from 150° to 250° C or without a catalyst at from 200° to 400° C. The molecular weight of the resulting oligomers is the lower, the higher is the polymerization temperature, and the more solvent and catalyst is present during the polymerization. In general, the oligomers of the monovinyl-aromatic compounds should have a molecular weight of from 300 to 30,000, the molecular weight range of from 400 to 8,000 being particularly advantageous. These data relate to the number-average molecular weight, determined by vapor pressure osmometry.

Only those oligomers of monovinyl-aromatic compounds which no longer contain any olefinic double bonds are employed in the process of the invention. Since the oligomers, as obtained from the process of synthesis, in most cases still contain olefinic double bonds, the latter must be removed by hydrogenation before the bromination is carried out. The selective hydrogenation of the olefinic double bonds in the oligomers of the monovinyl-aromatic compounds is carried out by conventional methods, using the conventional hydrogenation catalysts based on metals or salt of metals of group VIII of the periodic table. Suitable hydrogenation processes are described, e.g., in U.S. Pat. No. 3,113,986, German Published Application DAS No. 1,222,260 or German Laid-Open Application DOS No. 2,013,263. According to these publications, the hydrogenation can be carried out in a homogeneous phase with catalyst based on salts of cobalt, nickel or iron, which have been reduced with metal alkyls, at hydrogen pressures of from 1 to 100 bars and at from 25° to 150° C. Under these mild conditions, only selective hydrogenation of the olefinic double bonds takes place and the aromatic double bonds are not attacked. The hydrogenation of the olefinic double bonds in the oligomers should be carried out as completely as possible.

The bromination of the selectively hydrogenated oligomers, to be employed according to the invention, of the monovinyl-aromatic compounds is carried out in halogenated solvents, e.g. methylene chloride, chloroform, carbon tetrachloride, 1,1,2-trichloroethane, methylene bromide or 1,2-dibromoethane. In general, the selectively hydrogenated oligomers are dissolved in these halogenated solvents in amounts of from 5 to 40% by weight, based on the solution. Suitable catalysts for the bromination reaction are in particular the Lewis acids conventionally used for the nuclear halogenation of aromatic hydrocarbons. Examples which may be mentioned are iron, aluminum, iron-(III) chloride, iron-(III) bromide, aluminum chloride, aluminum bromide, copper bromide, antimony-(III) oxide or phosphorus halides. The use of aluminum chloride, iron chloride or metallic iron is particularly advantageous. Lewis acids are in general employed in amounts of from 0.1 to 10% by weight, preferably from 1 to 5% by weight, based on the end products. The bromination is carried out cold, employing reaction temperature of from $-25°$ C to $+20°$ C. As a rule, the bromination is carried out by adding the bromine slowly, whilst stirring, to the solution, also containing catalyst, of the selectively hydrogenated oligomers. The amounts of bromine added depend on the desired bromine content of the end product and are equivalent thereto. To complete the reaction, stirring of the mixture, after completion of the addition of bromine, can be continued at the reaction temperature and/or at room temperature.

The reaction solution is then worked up by first washing it with water, by conventional methods, until the wash water is neutral and free from bromide ions. A conventional sequence of extractions in the case of bromination reactions is first to extract the reaction solution with aqueous alkaline solutions and then with aqueous solutions of reducing agents, and thereafter to wash the solution with pure water. However, for working up the reaction solution produced according to the invention, such an extraction sequence can as a rule be dispensed with, i.e. in the case of the present invention it suffices, in most cases, to extract the reaction solution with water.

The brominated oligomer can be isolated from the reaction solution, which has been extracted with water, by conventional methods. Preferably, the reaction solution is freed from the solvent by evaporation; in general, temperatures above 200° C, and the use of reduced pressure, are necessary to remove the last remnants of solvent. The color of the resulting oligomer melts can be improved slightly by adding phosphites, which are advantageously introduced into the reaction solution after extraction with water but before evaporation of the solvent. Suitable color-improving agents are organic phoshites of sufficiently high boiling point; the latter should be above the temperature required to remove the solvent remnants from the reaction mixture and is advantageously above 240° C under reduced pressure. Suitable compounds are trialkyl phosphites, triaryl phosphites or cycloalkyl phosphites, and mixed aliphatic-aromatic phosphites, in all of which each individual alkyl, aryl or cycloalkyl should preferably be of 6 to 14 carbon atoms. The organic phosphites are added to the reaction solution in amounts of from 0.005 to 15% by weight, preferably from 0.1 to 0.5% by weight, based on the end product.

As a result of the particularly smooth course of the bromination reaction and the simple method which can be used to work up the reaction solution, yields of over 95% of theory can be achieved with the process of the invention. The bromine contents of the reaction product can be varied very widely. Thus, e.g., the selectively hydrogenated styrene oligomers can be brominated to give bromine contents of up to 71% by weight; at bromine contents higher than 71% by weight, the heat stability of the products rapidly declines. Accordingly, the bromine content of the heat-stable brominated oligomers, manufactured according to the invention, of the monovinyl-aromatic compounds is preferably from 0.5 to 71% by weight and especially from 4 to 65% by weight.

The heat-stable, brominated oligomers, according to the present invention, of the monovinyl-aromatic compounds are exclusively nuclear-brominated products which, at fairly high bromine contents, are in the form of colorless to yellowish solids of melting point 50°-250° C. On heating, they give colorless to red melts, and show no decomposition, due to elimination of hydrogen bromide, or discoloration, even at 240°-340° C. The brominated oligomers are highly heat-resistant and can be processed, by themselves or as components of mixtures with thermoplastics, to give various shaped articles. The brominated oligomers of the monovinyl-aromatic compounds can also be used, inter alia, as flameproofing agents for thermoplastics.

In the Examples which follow, parts and percentages are by weight, unless stated otherwise. The stated molecular weights of the hydrogenated oligomers are the number-average molecular weights determined by vapor pressure osmometry.

EXAMPLE 1

520 parts of a selectively hydrogenated oligostyrene which no longer contains any olefinic double bonds and has a molecular weight of 670, are dissolved in 2,100 parts of 1,1,2-trichloroethane. After adding 30 parts of AlCl$_3$, 800 parts of bromine are added dropwise in the course of 2 hours at from $-10°$ C to $-20°$ C. The reaction mixture is stirred from a further hours at from $-10°$ C to $-20°$ C and is then extracted about 4 times with water, until the wash water is neutral. 2.6 parts of tridecyl phosphite are then added to the reaction solution and the bulk of the solvent is distilled off at up to 150° C under normal pressure. The last remnants of solvent are removed under reduced pressure from a water-pump, at a bath temperature of 240° C. The melt is poured out whilst still hot, and is comminuted after it has solidified. 890 parts of a powder which contains 43.2% by weight of bromine and is slightly yellowish at room temperature are obtained. In a 1 cm thick layer, the melt shows a light yellow color, which does not deepen after heating for one hour at 320° C.

EXAMPLE 2

520 parts of an oligostyrene which has been hydrogenated until the olefinic double bonds are completely saturated and has a molecular weight of 1,100 are reacted with 800 parts of bromine by the method described in Example 1. The working up of the reaction solution, in addition of phosphite, are also carried out as described in Example 1. 870 parts of a very pale yellowish powder having a bromine content of 43% by weight are obtained; at 320° C, the material is in the form of a light yellow melt, the color of which does not deepen even after heating for one hour at 320° C.

EXAMPLE 3

Example 1 is repeated except that a selectively hydrogenated oligostyrene of molecular weight 450 is used. 880 parts of a yellow powder containing 42.8% by weight of bromine are obtained. The brominated oligomer is stable at 240° C and is in the form of a yellow melt at this temperature.

EXAMPLE 4

520 parts of a selectively hydrogenated oligostyrene of molecular weight 1,100, which no longer contains any olefinic double bonds, are reacted with 1,600 parts of bromine under the conditions described in Example 1. After extracting the reaction solution with dilute sodium hydroxide solution and water until the last wash water is neutral, and adding 2.6 parts of diphenyl isooctyl phosphite and distilling off the solvent, 1,120 parts of a yellow powder containing 60% of bromine are obtained; at 280° C, this material is in the form of a light yellow melt and shows no evolution of gas.

EXAMPLE 5

520 parts of a selectively hydrogenated oligostyrene of moleclar weight 1,100 are reacted with 2,400 parts of bromine in accordance with Example 1. In this case, 4 parts of tridecyl phosphite are added to improve the color. 1,540 parts of a powder containing 68.5% of bromine are obtained.

COMPARATIVE EXAMPLE 520 parts of a commercial polystyrene having a molecular weight of 100,000 are brominated as described in Example 1. After about 50% of the envisaged amount of bromine have been added, the addition is stopped since a sharp rise in viscosity is observed. Shortly afterward, the reaction mixture reaches a completely crosslinked state.

We claim:

1. A process for the manufacture of heat-stable, brominated oligomers of monovinyl-aromatic compounds which comprises:

dissolving selectively hydrogenated oligomers of the monovinyl-aromatic compounds a halogenated solvents; reacting the hydrogenated oligomers with bromine in the presence of a Lewis acid catalyst at a temperature of from $-25°$ C to $+20°$ C while starting the reaction solution; washing the reaction solution with water to eliminate bromide ions; and thereafter isolating the brominated reaction product from the reaction solution.

2. A process as set forth in claim 1, in which the selectively hydrogenated oligomers of the monovinyl-aromatic compounds have a molecular weight of from 400 to 8,000 before bromination.

3. A process set forth in claim 1, in which the selectively hydrogenated oligomers of the monovinyl-aromatic compounds are brominated to a bromide content of from 0.5 to 71% by weight.

4. A process set forth in claim 1, in which from 0.005 to 15% by weight of a high-boiling organic phosphite are added to the reaction solution after extraction with water but before isolating the brominated reaction product.

5. A process as set forth in claim 1 wherein the monovinyl-aromatic compound is a homo-oligomer of styrene.

* * * * *

UNITED STATES PATENT AND TRADEMARK OFFICE
CERTIFICATE OF CORRECTION

PATENT NO. : 4,074,032

DATED : February 14, 1978

INVENTOR(S) : Herbert Naarmann et al

It is certified that error appears in the above-identified patent and that said Letters Patent are hereby corrected as shown below:

Column 6, line 11, "a" should read --in--.

Signed and Sealed this

Twenty-second Day of August 1978

[SEAL]

Attest:

RUTH C. MASON
Attesting Officer

DONALD W. BANNER
Commissioner of Patents and Trademarks